United States Patent
Doswell et al.

(10) Patent No.: US 10,204,213 B2
(45) Date of Patent: Feb. 12, 2019

(54) METHODS AND APPARATUS FOR MONITORING AND/OR REGULATING MEDICAMENT AND MEDICAMENT DISPENSATION

(71) Applicants: Jayfus T. Doswell, Baltimore, MD (US); Kimberly Michele Armstrong, Baltimore, MD (US)

(72) Inventors: Jayfus T. Doswell, Baltimore, MD (US); Kimberly Michele Armstrong, Baltimore, MD (US)

(73) Assignees: Jayfus T. Doswell, Baltimore, MD (US); Kimberly Michele Armstrong, Baltimore, MD (US)

(*) Notice: Subject to any disclaimer, the term of this patent is extended or adjusted under 35 U.S.C. 154(b) by 503 days.

(21) Appl. No.: 14/968,226

(22) Filed: Dec. 14, 2015

(65) Prior Publication Data
US 2017/0169184 A1    Jun. 15, 2017

(51) Int. Cl.
*G06F 19/00* (2018.01)
*A61B 5/0488* (2006.01)
*A61B 5/00* (2006.01)
*A61B 5/11* (2006.01)
*A61M 15/00* (2006.01)

(52) U.S. Cl.
CPC ........ *G06F 19/3456* (2013.01); *A61B 5/0488* (2013.01); *A61B 5/1112* (2013.01);
(Continued)

(58) Field of Classification Search
CPC ......... G06Q 50/22–50/24; G16H 10/00; G06F 19/30; G06F 19/3456; G06F 19/00;
(Continued)

(56) References Cited

U.S. PATENT DOCUMENTS

| | | | |
|---|---|---|---|
| 2007/0276270 A1* | 11/2007 | Tran | A61B 5/0022 600/508 |
| 2011/0225008 A1* | 9/2011 | Elkouh | G06F 21/6245 705/3 |
| 2012/0194976 A1* | 8/2012 | Golko | G06F 1/163 361/679.01 |

(Continued)

OTHER PUBLICATIONS

Patel, S. Quantitative motor assessment in patients with mobility limiting conditions using wearable sensors (Order No. 3507186). Available from ProQuest Dissertations & Theses Global. (1015627346). Retrieved from https://search.proquest.com/docview/1015627346?accountid=14753. (Year: 2012).*

*Primary Examiner* — Robert A Sorey
(74) *Attorney, Agent, or Firm* — Eversheds Sutherland (US) LLP

(57) ABSTRACT

Some embodiments are directed to a system for monitoring an inhaler that includes a volume of medicament for dispensation to an individual. The system includes a transmitter, disposed at the inhaler, for wirelessly transmitting data relating to the aspect of the inhaler. A monitor, which is remote from the transmitter and the inhaler, includes a receiver for receiving the data wirelessly transmitted from the transmitter, the data relating to the aspect of the inhaler including positional data relating to a relative position of the inhaler relative to the monitor and in particular a distance separating the inhaler and the monitor. The monitor also includes a processor for determining whether the distance separating the inhaler and the monitor exceeds a predetermined distance, the processor causing actuation of a notification device upon determining that the distance separating the inhaler and the monitor exceeds the predetermined distance.

3 Claims, 3 Drawing Sheets

(52) U.S. Cl.
CPC ............ *A61B 5/4833* (2013.01); *A61B 5/742* (2013.01); *A61M 15/009* (2013.01); *G06F 19/00* (2013.01); *A61B 2562/0219* (2013.01); *A61M 2205/3561* (2013.01); *A61M 2205/3592* (2013.01); *A61M 2205/582* (2013.01); *A61M 2209/01* (2013.01); *A61M 2209/088* (2013.01)

(58) Field of Classification Search
CPC ... A61B 5/0488; A61B 5/1112; A61B 5/4833; A61B 5/742; A61M 15/009
See application file for complete search history.

(56) References Cited

U.S. PATENT DOCUMENTS

| | | | |
|---|---|---|---|
| 2015/0366504 A1* | 12/2015 | Connor | A61B 5/6804 600/301 |
| 2016/0021535 A1* | 1/2016 | Tali | H04W 68/00 455/411 |
| 2016/0082208 A1* | 3/2016 | Ballam | A61M 16/0003 128/200.14 |
| 2016/0144141 A1* | 5/2016 | Biswas | A61M 15/009 128/200.23 |
| 2016/0150362 A1* | 5/2016 | Shaprio | H04W 4/02 340/539.13 |
| 2016/0171863 A1* | 6/2016 | Murrell | G08B 21/0269 340/539.13 |
| 2016/0174857 A1* | 6/2016 | Eggers | G06F 19/3418 600/301 |
| 2016/0321901 A1* | 11/2016 | Desoyza | A61B 5/747 |
| 2016/0354562 A1* | 12/2016 | Morrison | A61M 15/0001 |

* cited by examiner

METHODS AND APPARATUS FOR MONITORING AND/OR REGULATING MEDICAMENT AND MEDICAMENT DISPENSATION

BACKGROUND

Field of Invention

Some embodiments are directed to methods and apparatus for monitoring and/or regulating medicament and medicament dispensation. In particular, some embodiments are directed to: 1) monitoring or tracking medicament location; 2) providing indications based on the monitored medicament location; 3) monitoring administration techniques for various types of medicament; 4) monitoring amounts of medicament delivered; and/or 5) gathering data regarding the monitored locations and/or activities, and/or utilizing any or all of this data in any beneficial or useful manner.

Background

Proximity to medicament may be a prerequisite to achieving the benefits provided thereby. For example, it may be difficult or impossible to administer certain types of medicament to an individual (hereinafter patient) who is intended to benefit from the medicament if the patient is not in proximity thereto. In other words, a patient needs to be in proximity to certain types of medicament for administration thereof, such as for medicaments that are administered directly to the patient, e.g., medicaments taken orally, intravenously, inhaled, etc.

In addition, using improper administration techniques may result in administration of an improper, imprecise, inconsistent dosage(s) of medicament, and rate(s) of administration of medicament, which may negatively affect achievement of intended benefits of the medicament, patient health, etc. This issue may be especially relevant in the context of medicines that are administered regularly over relatively long periods, and/or administered by non-skilled caregivers, semi-skilled caregivers, or the patients themselves.

These and/or other issues are prevalent with regard to a number of different types of medicaments and/or medical conditions, including but not limited to inhalers for asthma. As discussed in detail below, certain groups of patients are especially at risk of failing to achieve the intended benefits of these types of medicament.

Some of the issues that are relevant to accurate asthma compliance with regard to children include: 1) children tend to leave their location (e.g., house, etc.,) without or lose asthma inhalers; 2) parents, guardians, and pediatricians experience difficulty accurately and remotely monitoring asthma inhaler medication compliance and dosage rates; 3.) children tend to apply improper inhaler techniques; and 4.) children tend to practice intentional non-compliance. These problems alone increase asthma exacerbations, which may lead to increased emergency department visits, primary health care costs, etc.

This issue is especially problematic based on this condition being incredibly widespread. Childhood asthma in the United States (U.S.) has skyrocketed in the last two decades, and disadvantaged children suffer disproportionately more than any other group of children in the U.S. According to the Center for Disease Control (CDC), one in 12 people (i.e., ~25 million or 8% of the population) were diagnosed with asthma in 2009, compared with 1 in 14 (~20 million, or 7%) in 2001. In 2008, 57% more children suffered an asthma attack and also more than 51% adults. More disturbingly, 1,857 children and 3,262 adults died from asthma in 2007. Among persons suffering from asthma, disadvantaged children are hardest hit.

In the U.S., the dollar figure placed on the direct and indirect costs of patient noncompliance with regard to various types of medication is estimated to be at $1.3 billion per year. This figure includes the cost of additional doctor visits, emergency room visits, hospitalizations, additional medications, complications, disease progression, premature disability, and death.

Research studies indicate that costs attributed to asthma exacerbation are significant, both directly and indirectly. Emergency hospitalizations and medications account for the greatest percentage of direct costs, while child absenteeism accounts for the greatest percentage of indirect costs. In Baltimore, Md., the average cost per asthma emergency room visit for children is $820, and the average hospitalization stay from asthma exacerbation is 3.8 days. In the U.S., medical expenses for people who suffer from asthma each year cost $3,300 per person from 2002 to 2007. Medical expenses, associated with asthma increased from $48.6 billion in 2002 to $50.1 billion in 2007. Furthermore, approximately 40% uninsured people with asthma cannot afford their prescription medication, in comparison to about 11% insured people. In 2008, 59% of children and 33% of adults suffered an asthma attack missed school or work. On average, children missed 4 days of school and adults missed 5 days of work because of asthma.

SUMMARY

It may therefore be relevant to monitor or otherwise determine medicament location, such as the location of the medicament relative to the patient. For example, determining medicament location may useful in a variety of ways, such as with regard to medicaments that need to be in proximity to patients for their administration, e.g., for medicaments that are administered directly to the patient (medicaments taken orally, intravenously, inhaled, etc.).

Data gleaned from this type of monitoring may be used to enhance a patient's ability to have access to the medicament, such as by facilitating the patient's ability to remain proximate the medicament. In some such cases, this data can be used to notify the patient if a distance separating the patient and the medicament exceeds a certain amount. For example, the patient may be notified if the patient travels from a location from which the patient has unintentionally left the medicament.

Embodiments are intended to include or otherwise cover any methods and apparatus for providing this notification. In some embodiments, the user is provided with a wristband or other wearable device that provides this notification. The notification can be provided in any form or combination of forms, such as visual, audio, tactile (vibration), etc.

This type of notification may be beneficial by informing the patient that the patient has unintentionally left the medicament at a location and is currently traveling away from the medicament. The user may thereby be reminded to return to that location and reclaim the medicament.

It may also be relevant to monitor or otherwise determine whether proper administration techniques are being followed or otherwise used for the administration of many different types of medicament in a variety of contexts. For example, certain types of medicaments are configured for administration using specific procedures that negatively affect patient health if not followed properly. In one example, asthma inhalers need to be manipulated into a certain orientation relative to the patient (such as to the patient's mouth) to achieve proper dosages, rates of dosages, etc. asthma inhalers also need to be actuated in a certain manner to achieve the intended benefits. For example, an asthma inhaler trigger needs to be depressed with a certain amount of force and for a certain period in order to dispense medicament at an appropriate dosage, rate, etc.

Some embodiments are therefore directed to methods and apparatus for monitoring the orientation of asthma inhalers during usage. The data gleaned from this usage can be used for a variety of purposes. For example, this data can be used to notify the patient and/or others that the asthma inhaler is not in an appropriate orientation during administration. The patient and/or others can use this notification to thereby modify the orientation to achieve an enhanced orientation and thereby positively affect the medicament dosage, dosage rate, etc.

Some embodiments are also directed to methods and apparatus for monitoring asthma inhaler actuation, and in particular actuation of the trigger needs to be depressed with a certain amount of force and for a certain period in order to dispense medicament at an appropriate dosage, rate, etc. This data can be used to notify the patient and/or others that the trigger is not being properly actuated. The patient and/or others can use this notification to thereby modify the trigger actuation to achieve an enhanced actuation and thereby positively affect the medicament dosage, dosage rate, etc.

Some embodiments are directed to portable and/or wearable apparatus that interact with medicament containers to address some or multiple of the issues discussed above. More specifically, some embodiments are directed to portable and/or wearable asthma monitors that monitor personal asthma inhalers, and facilitate compliance with the medication usage for the treatment of asthma.

Some of these embodiments enable are particularly helpful for certain groups, such as children, to better assist their managing asthma Inhaler compliance, and/or care providers, parents, guardians, etc., track the asthma compliance of children for which they are responsible. As discussed above, some embodiments can be used so that the patient may: 1) receive visual, audio, and/or vibration notifications (such as via a wristband) if the child/wristband is disposed far away from the relevant asthma inhaler; 2) track asthma dosage compliance without or with reduced physical modification of the asthma inhaler drug canister; 3.) Track proper and/or improper asthma inhaler techniques; and/or 4.) transmit this data to a database for any appropriate usage.

Thus, some of the above embodiments involve methods and apparatus that achieve or provide one or more of the following: low cost implementation, enhanced asthma management and dose tracking, enhanced compliance tracking, web and/or cloud based monitoring, enhanced use tracking, patient reminders based on location and/or administration techniques, loss reduction and/or prevention, GPS/Bluetooth asthma tracking, short range wireless tracking, and/or data management and communication.

Some of these advantages are provided by a system for monitoring an inhaler that includes a volume of medicament for dispensation to a patient. The system includes a notification device for providing a notification to the patient regarding an aspect of the inhaler, and a transmitter, disposed at the inhaler, for wirelessly transmitting data which includes the aspect of the inhaler. A monitor, which is remote from the transmitter and the inhaler, includes a processor and a receiver for receiving the data wirelessly transmitted from the transmitter, the data relating to the aspect of the inhaler including positional data relating to a relative position of the inhaler relative to the monitor and in particular a distance separating the inhaler and the monitor. The processor of the monitor determines whether the distance separating the inhaler and the monitor exceeds a predetermined distance, the processor causing actuation of a notification device upon determining that the distance separating the inhaler and the monitor exceeds the predetermined distance.

DETAILED DESCRIPTION

Figure 1:
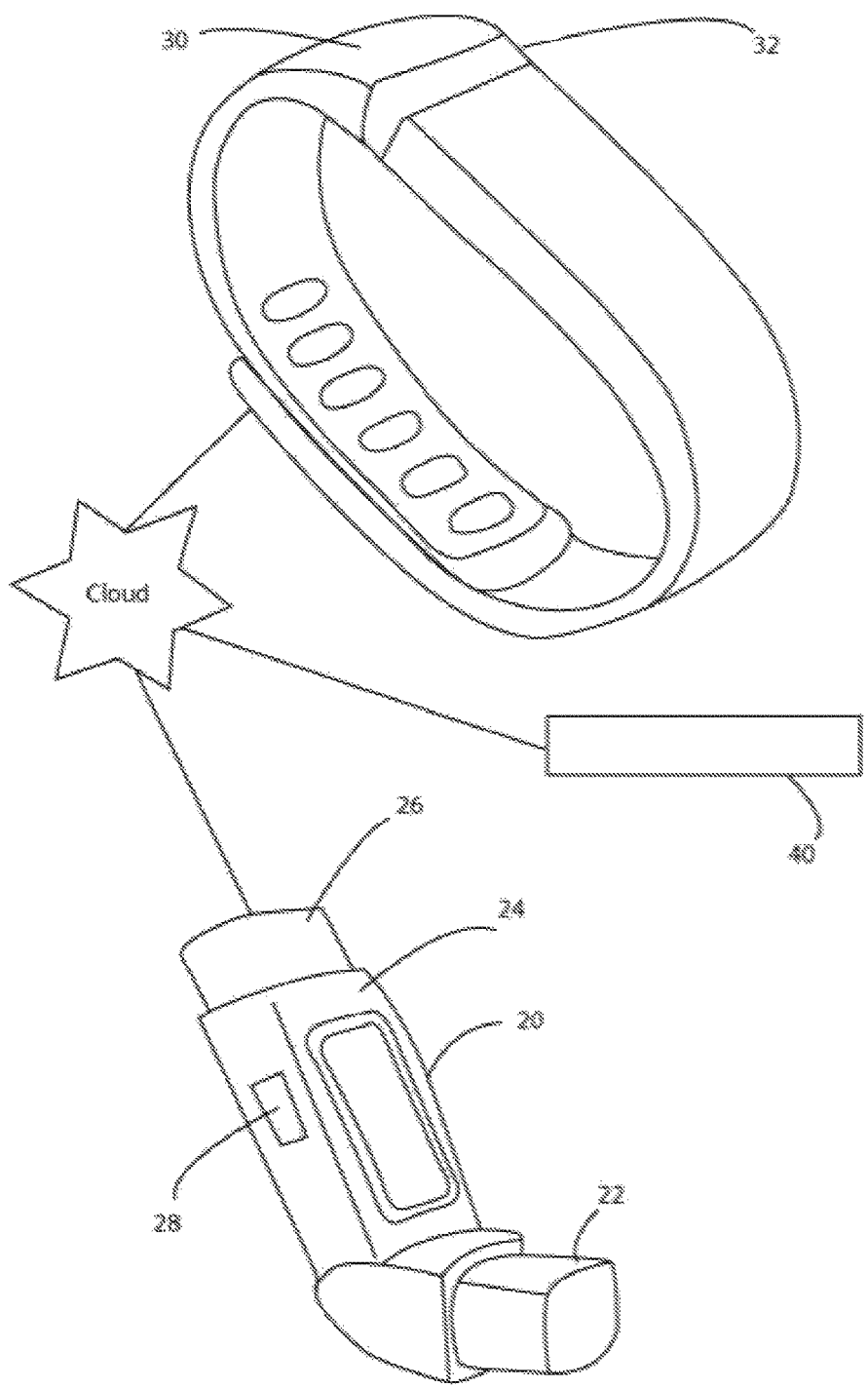
FIG. 1 is schematic of a monitoring system in accordance with some embodiments, including a monitor and an asthma inhaler.

It is to be understood that the various embodiments are not limited by the details of construction and the arrangement of components set forth in the following description or illustrated in the drawings.

Some of the embodiments are disclosed below in the context of a wearable monitor (such as a wristband) that provides at least one of the following: 1) notifies the patient that the patient has traveled a distance that is too far away from an asthma inhaler; 2) tracks asthma dosage compliance, such as with reduced or even without physical modification of the asthma inhaler medical dispenser; 3) wirelessly transmits relevant data without the need for additional transmitters, such as a smart phone, etc.

However, embodiments are intended to include or otherwise cover any form of portable monitor in addition to or other than a wristband. In addition, embodiments are intended to include or otherwise cover performing any of the above operations in contexts other than the administration and monitoring of asthma inhalers. For example, some embodiments directly relate to and address administration and monitoring of other types of medicaments and/or other medical conditions. In fact, some embodiments can be usable in non-human medical applications, such as with regard to veterinary applications. Still further, some embodiments are directed to administration and monitoring of apparatus used in non-therapeutic or non-medical applications.

I. Monitoring System

FIG. 1 is schematic of a monitoring system 10 in accordance with some embodiments, including a monitor 30 and an asthma inhaler 20. Certain basic features of the inhaler 20 and monitor 30 are discussed below.

The inhaler 20 can be formed of multiple separate elements. For example, the inhaler 20 can include a medicament exit aperture 22 through which medicament exits a medicament storage canister (not shown) that is disposed within an inhaler housing 24. In other words, the medicament can be stored within a medicament storage canister that is disposed within the inhaler housing 24, and the medicament exits via the medicament exit aperture 22 when released. In some cases, the medicament exit aperture 22 is placed within a mouth of a patient so that the medicament released travels into the patient's mouth and into the patient's respiratory system via the medicament exit aperture 22.

The inhaler 20 also includes a trigger 26 that is manually depressible to cause the release of the medicament from the medicament storage canister. For example, the trigger 126 can be manually depressed toward the inhaler housing 24 and thereby travel within the inhaler housing 24 based on cooperating telescoping structures. This movement within the inhaler housing 24 actuates a valve mechanism to release the medicament from the medicament storage canister. The trigger 26 can be biased so that removal of the depressing force (or a sufficient reduction in this force) causes the trigger 26 to return to its at rest position shown in FIG. 1, which thereby actuates the valve mechanism to impede or prevent the release of the medicament from the medicament storage canister.

Embodiments are intended to include or otherwise cover any structure of combination of structures that enable or facilitate the above operations. For example, some embodiments include additional or alternative structures to perform the operations disclosed above with regard to any or all of the above inhaler elements.

The inhaler 20 also includes a transmitter 28 that transmits certain information that is relevant to the inhaler 20. In some embodiments, the transmitter 28 includes a positioning mechanism that provides locational data, and transmits that locational data to a receiver of the monitor 30. This locational data may be especially important in determining or otherwise monitoring the location of the inhaler 20 relative to the monitor 30, and thus in these embodiments the monitor 30 includes a similar positional mechanism that provides locational data of the monitor 30.

In some of these embodiments, the monitor 30 notifies the patient if the monitor 30 and inhaler 20 become separated by more than a certain distance. This feature may be especially helpful for informing the patient that the patient has unintentionally left the inhaler 20 at a certain location and is currently traveling away from the inhaler. The user may thereby be reminded to return to that location and reclaim the inhaler. This feature thereby enhances the patient's ability to have access to the medicament, such as by facilitating the patient's ability to remain proximate the medicament.

Embodiments are intended to include or otherwise cover positioning mechanisms that utilize any and all known, related art or later developed technologies for determining the location of the relative locations of the inhaler 20 and the monitor 30, including GPS technologies. In other embodiments, the locations of the inhaler 20 and the monitor 30 are not separately determined, and instead the inhaler 20 (using at least in part the transmitter 28) transmits a wireless signal to the receiver of the monitor 30, and aspects of this signal are used to determine the relative positions of these devices.

In other embodiments, the transmitter 28 transmits additional or alternative data to the monitor. For example, the monitor 30 can track the orientation of the inhaler 20 through the use of, for example, a gyroscope; and the transmitter can transmit the data relating to the orientation of the inhaler, such as when the inhaler 20 is administrating medicament.

The data transmitted regarding inhaler 20 orientation can be used for a variety of purposes. For example, this orientation data can be used to notify the patient and/or others that the asthma inhaler is not in an appropriate orientation during administration. The patient and/or others can use this notification to thereby modify the orientation to achieve an enhanced orientation and thereby positively affect the medicament dosage, dosage rate, etc.

In still other embodiments, the transmitter 28 transmits additional or alternative data to the monitor, including data regarding inhaler 20 actuation. This data can be relate to trigger 26 actuation, and in particular the amount of force applied to the trigger 26 (and in particular the linear distance of movement of the trigger 26), as well as the period in which the force is applied to the trigger 26 (i.e., the time that the trigger 26 is depressed), both of which affect dosage amount, dosage rate, etc.

This data can be used to notify the patient and/or others that the trigger 26 is not being properly actuated. The patient and/or others can use this notification to thereby modify the trigger 26 actuation to achieve an enhanced actuation, and thereby positively affect the medicament dosage, dosage rate, etc.

However, the above types of data are merely provided for exemplary purposes. Embodiments are intended to include or otherwise cover transmission of any type of data relating to any aspect of the inhaler 20 and/or data relating to a relationship between the inhaler 20 and the monitor 30 that may be helpful.

As shown in FIG. 1, the monitor 30 can transmit the data that it receives from the inhaler 20 to a central station 40, such as via the cloud 42. This data can be used by the central station 40 for any beneficial purpose, such as to monitor a specific patient for the benefit of that specific patient. In addition or as an alternative, the central station 40 can use this data for a variety of other reasons, such as maintain statistics on multiple patients, perform analytics using this data, etc.

Embodiments are intended to include or otherwise cover transmitting other types of data to the central station 40. For example, the monitor 30 can process or perform analytics on the data that it receives from the inhaler 20, and transmit this processed data or data relating to the analytics to the central station 40, which can use this data for any beneficial purpose.

Embodiments are intended to include or otherwise cover any and all known, related art, or later developed technologies for wirelessly transmitting the data from the monitor 30 to the central station 40. For example, some embodiments are not cloud based and instead use other technologies for this transmission.

Furthermore, for a user that utilizes multiple inhalers, each user may register a monitor 30. Each inhaler 20 can have one unique Radio Frequency Identifier (RFID) 28 containing a unique ID. The monitor 30 will be registered to one or more inhalers tagged with their respective RFID. For each inhaler 20 tagged with one RFID and containing a unique ID, the unique ID will be stored in remote database. If the monitor 30 is at a pre-defined distance far away from a RFID tagged inhaler 20 and its contained RFID reader transmits a signal without receiving the expected RFID data back, then the monitor 30 may vibrate to notify that the user is out of range from an inhaler; and hence, may be interpreted as being left behind.

II. Monitor 30

Figure 2:
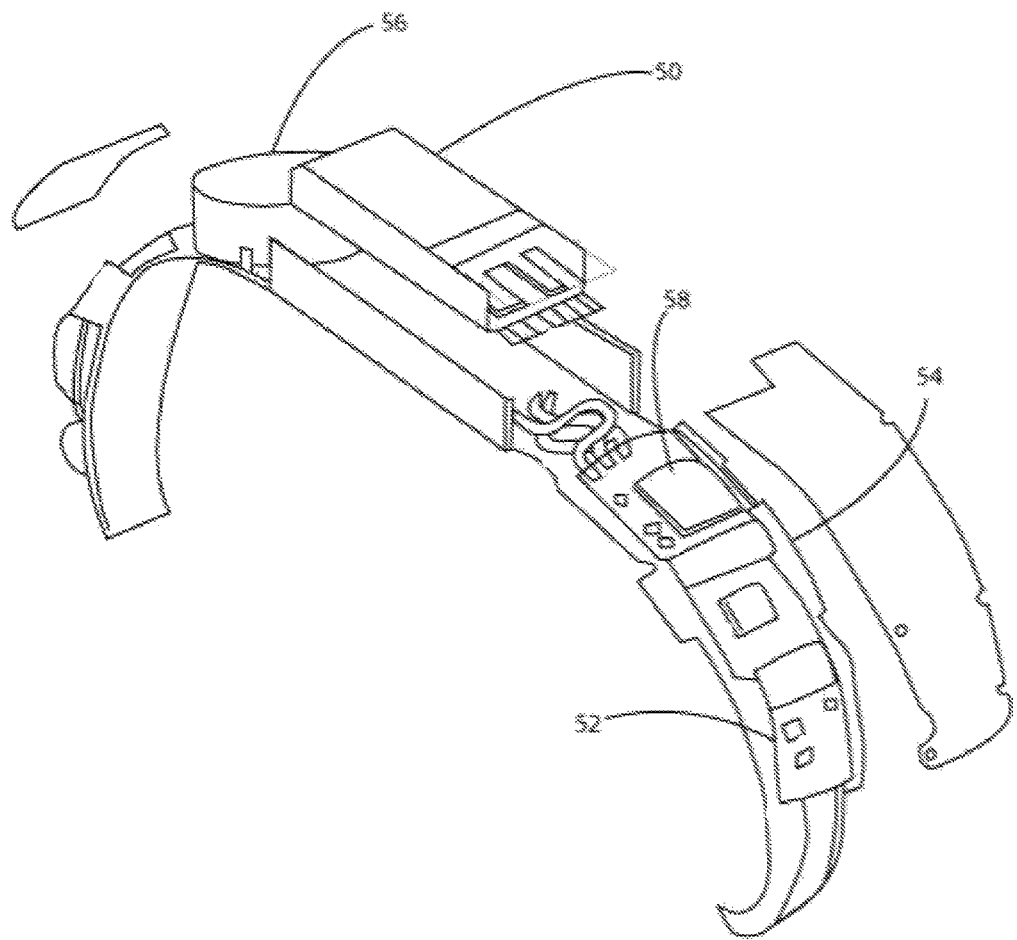
FIG. 2 is an exploded perspective view of the monitor of FIG. 1.

FIG. 2 is an exploded perspective view of the monitor of FIG. 1. In particular, the monitor 30 of FIG. 1 is shown with an exterior cover removed and various of its components separated from their mounted locations.

As shown in FIG. 2, the monitor 30 includes a battery 50 that provides a source of electric power to the monitor 30. Embodiments are intended to include or otherwise cover any type of known, related art, and/or later developed battery technology. In some embodiments, the battery 50 is rechargeable, which may be beneficial for convenience, i.e., so that the user does not need to replace the battery or monitor 30.

The monitor 30 also includes an inertia sensor 52, such as a gyroscope and/or accelerometer. The inertia sensor 52 can be used to determine the location and/or orientation of the monitor 30. For example, the inertia sensor 52 can collect gyroscope (i.e., roll, pitch and yaw) data across acceleration at the X, Y, Z axis. The monitor 30 includes a processor or microcontroller 58 to interpret and process the gyroscope data in order to track the proper angle of use of the inhaler 20. Embodiments are intended to include or otherwise cover any and all known, related art or later developed technologies for determining the location and/or orientation of the monitor 30.

The monitor 30 also includes a surface electromyogram (sEMG) sensor 54 that non-invasively collects muscle data (e.g., electrical muscle signals) from, for example, the patient's wrist. The sEMG sensor 54 can be used to determine how much force is applied to the trigger 26 of the inhaler 20, and/or how long this force is applied. For example, the monitor's microcontroller 58 interprets collected motor unit action potential (MUAP) and converts it to a corresponding computer data format when the user depresses the inhaler 26. The monitor 30 then matches the collected MUAP data against a pre-defined MUAP data range to uniquely determine if an inhaler 26 depress was actually achieved and correctly performed. Embodiments are intended to include or otherwise cover any and all known, related art or later developed technologies for determining how much force is applied to the trigger 26 of the inhaler 20, and/or how long this force is applied.

In some embodiments, one or more of the sEMG sensors 54, which are encapsulated in the monitor 30, are provided with capabilities interacting with embedded software to identify when the patient depresses the trigger 26 of the inhaler. Thus, the sEMG sensors 54 are able to track an inhaler 30 compliance event.

The monitor 30 also includes a vibration motor 56 that provides an indication to the patient of at least one condition. For example, the vibration motor 56 can cause a vibration that is perceivable to the patient to notify the patient that the distance separating the inhaler 20 and the monitor 30 has exceeded a certain distance. This vibration can alternatively or additional be applied under other conditions, such as where the inhaler 30 is being administered improperly, such as at an erroneous orientation, or where the trigger 26 is being actuation with an erroneous amount of force and/or the force is being applied for an erroneous period. Embodiments are intended to include or otherwise cover any and all known, related art or later developed technologies for causing the vibrations discussed above.

Other types of notifications and be provided in addition, or as an alternative to, the vibrations discussed above. For example, FIG. 1 shows that the monitor 30 includes a light 32 that is located at a position on the monitor 30 to be recognizable to a patient wearing the monitor 30 on the patient's wrist. The light 32 can be used to notify the patient of any of the conditions disclosed herein. In addition, the light 32 can be used to communicate, or otherwise provide output as a function of, band activity.

The processor or microcontroller 58 of the monitor 30 processes and/or stores the EMG data and/or other data. For example, the processor processes the data discussed above and performs the operations discussed above. Embodiments are intended to include or otherwise cover any and all known, related art or later developed technologies for processing and storing the data discussed above.

The monitor 30 may be in the form of a wrist band so as to be easily worn on a user's wrist. However, the monitor 30 may take the form of any shape that may be worn by a user and operate as discussed herein to determine the location and/or orientation of the monitor 30, non-invasively collects muscle data, determine how much force or how long force is applied to the trigger 26 of the inhaler 20, etc.

III. Method Of Operation

Figure 3:
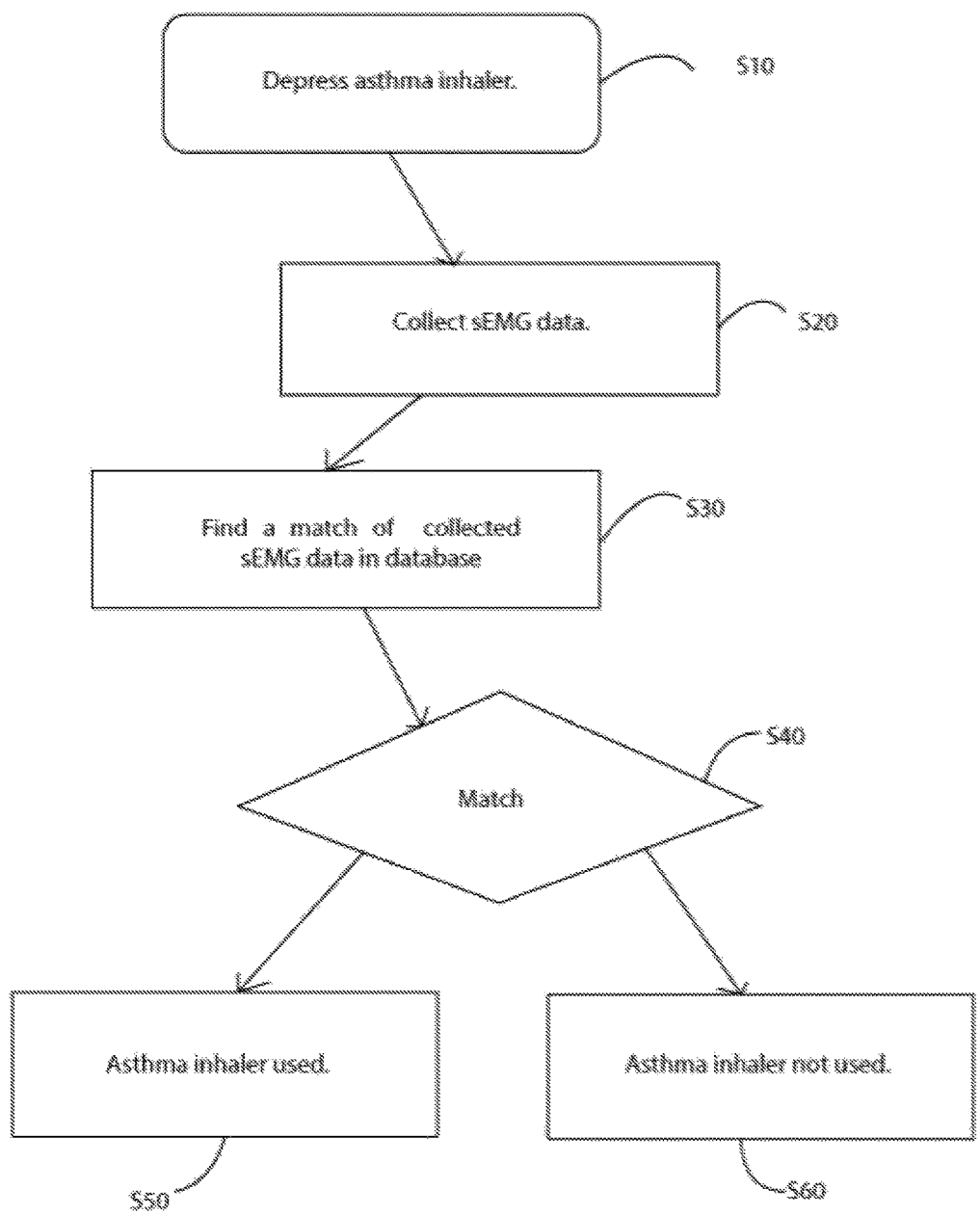
FIG. 3 is a flowchart of an exemplary method of operation of the apparatus shown in FIG. 1.

FIG. 3 is a flowchart of an exemplary method of operation of the apparatus shown in FIG. 1. A user may depress the inhaler as shown at step S10. Data may be collected with the sEMG sensor as shown at step S20. For example, the monitor 30 with the sEMG sensor 54 may collect electrical muscle signals from, for example, a user's wrist. The data collected by the sEMG sensor 54 may be compared to a database, as shown at step S30. A determination may be made as to whether there is a match between the collected data and data in the database, as shown at step S40. Finally, a determination as to whether the asthma inhaler has been used or not used may be made, as shown at steps S50 and S60.

IV. Alternative Embodiments

The microcontroller 58 of the monitor 30 can be structured to obviate an external process required by related technologies, such as a mobile phone. For example, the microcontroller 58 can be programmed with software so that it can operate as a mobile computer software application ("App") to display an easy to understand graphical user interface (GUI), the inhaler medical compliance, and position technique metrics to App subscribers including the wearer (i.e., child), parent/guardian, and pediatricians. However, other embodiments of the system 10 include additional or alternative elements to perform additional or alternative operations.

This system can be designed as a server based Software as a Service (Saas) (i.e., cloud service) to provide a federation of software intelligent agents to process data from large numbers of users. The central station 40 can collect and store daily compliance and inhaler technique data for each user (e.g., child). For each user, the central station 40 can also store points to incentive patients to continually use their inhalers when linked with the disclosed system. However, other embodiments of the system 10 include additional or alternative elements to perform additional or alternative operations.

The sEMG sensor 54 can be structured to non-invasively detect and collect myograph signals in the wrist and send to the microcontroller to convert into a digital equivalent and subsequently, store and interpret to determine, uniquely, if the forefinger movement at a measurably accurate pressure depressed an inhaler button to dispense the asthma inhaler medication. However, other embodiments of the sEMG sensor 54 can be structured differently to perform additional or alternative operations.

What is claimed is:

1. A system for monitoring an inhaler that includes a volume of medicament for dispensation to an individual, the system comprising:

an inhaler comprising a housing for receiving a medicament storage canister and comprising a trigger, and a transmitter for wirelessly transmitting data comprising a location of the inhaler;

a wearable monitor which is configured to be worn on the individual's wrist and which comprises:
 a receiver for receiving the data wirelessly transmitted from the transmitter,
 an inertia sensor comprising a gyroscope and an accelerometer configured to track orientation of the inhaler during actuation of the trigger, a surface electromyogram (sEMG) sensor configured to collect muscle data from the individual's wrist corresponding to the force and duration of actuation of the trigger, a microprocessor configured to
- compare an orientation of the inhaler while dispensing the volume of medicament with a predefined dispensing orientation,
- compare an applied trigger pressure and duration with a pre-defined motor unit action potential data range, including a predefined trigger pressure and trigger duration, wherein the predefined trigger pressure and trigger duration are obtained from the muscle data, and
- determine whether a distance separating the inhaler and the wearable monitor exceeds a predetermined distance, and a vibration motor and light which are configured to notify the individual of (i) an erroneous inhaler orientation, (ii) an erroneous actuation of the trigger, and (iii) excessive separation distance between the inhaler and the monitor, thereby permitting the individual to adjust use or location of the inhaler.

2. A system for tracking inhaler usage techniques comprising:

an inhaler comprising a housing for receiving a medicament storage canister and comprising a trigger, a positioning mechanism providing locational data, and a transmitter for wirelessly transmitting data comprising a location of the inhaler; and a wearable monitor configured to be worn on an individual's wrist and which comprises:
- a receiver for receiving the data wirelessly transmitted from the transmitter,
- an inertia sensor comprising a gyroscope and an accelerometer configured to track orientation of the inhaler during actuation of the trigger,
- a surface electromyogram (sEMG) sensor configured to collect muscle data from the individual's wrist corresponding to the force and duration of actuation of the trigger, and
- a microprocessor configured to
  - compare an orientation of the inhaler while dispensing medicament with a predefined dispensing orientation,
  - compare an applied trigger pressure and duration obtained from the muscle data with a predefined trigger pressure and trigger duration,
  - determine whether a distance separating the inhaler and the wearable monitor exceeds a predetermined distance, and
  - notify the individual of (i) an erroneous inhaler orientation, (ii) an erroneous actuation of the trigger, and (iii) excessive separation distance between the inhaler and the monitor, thereby permitting the individual to adjust use or location of the inhaler.

3. The system of claim 2, wherein the monitor further comprises a light and a vibration motor configured to provide said notifying.

\* \* \* \* \*